United States Patent [19]

Massey

[11] Patent Number: 4,704,407
[45] Date of Patent: Nov. 3, 1987

[54] SOLUBLE DOBUTAMINE SALTS

[75] Inventor: Eddie H. Massey, Indianapolis, Ind.

[73] Assignee: Eli Lilly and Company, Indianapolis, Ind.

[21] Appl. No.: 914,962

[22] Filed: Oct. 3, 1986

Related U.S. Application Data

[63] Continuation of Ser. No. 684,404, Dec. 20, 1984, abandoned.

[51] Int. Cl.[4] .................. C07C 87/28; A61K 31/135
[52] U.S. Cl. ............................ 514/649; 260/501.1; 564/381
[58] Field of Search ............... 260/501.1; 564/381; 514/649

[56] References Cited

U.S. PATENT DOCUMENTS

| | | | |
|---|---|---|---|
| 2,276,619 | 3/1942 | Kulz | 260/570.8 |
| 2,949,359 | 8/1960 | Blout et al. | 96/66 |
| 3,139,441 | 6/1964 | Biel | 260/340.5 |
| 3,410,944 | 11/1968 | Claassen et al. | 260/501.1 |
| 3,485,873 | 12/1969 | Aceto et al. | 260/501.1 |
| 3,502,723 | 3/1970 | Miller et al. | 260/501.1 |
| 3,539,613 | 11/1970 | Galvin et al. | 260/501.1 |
| 3,547,999 | 12/1970 | Shulgin | 260/501.1 |
| 3,700,692 | 10/1972 | Suh | 424/282 |
| 3,932,461 | 1/1976 | Suh | 424/282 |
| 3,987,200 | 10/1976 | Tuttle et al. | 424/330 |

OTHER PUBLICATIONS

Ariens, *Proc. Inter. Pharmacol. Meeting,* 7, 247–64 (1961).

*Primary Examiner*—Glennon H. Hollrah
*Assistant Examiner*—Raymond Covington
*Attorney, Agent, or Firm*—Charles W. Ashbrook; Leroy Whitaker

[57] ABSTRACT

Hydroxyalkanoic or alkandioic acid salts of dobutamine having desirable water solubility, useful in preparing intravenous solution for treatment of cardiogenic shock.

27 Claims, No Drawings

SOLUBLE DOBUTAMINE SALTS

This application is a continuation of application Ser. No. 684,404, filed Dec. 20, 1984, now abandoned.

BACKGROUND OF THE INVENTION

Dobutamine, (±)-N-[3-(4-hydroxyphenyl)-1-methylpropyl]2-(3,4-dihydroxyphenyl) ethylamine is marketed as the hydrochloride salt under the trademark Dobutrex ®. The use of dobutamine as an inotrope useful for treating cardiac insufficiency is disclosed and claimed in U.S. Pat. No. 3,987,200 which describes only mineral acid salts of dobutamine. Kulz, U.S. Pat. No. 2,273,619, discloses a higher homologue of dobutamine, N-[3-(4-hydroxyphenyl)-1-methylpropyl]-1-methyl-2-(3,4-dihydroxyphenyl) ethylamine (Example 1) and an isomer, N-[3-(4-hydroxyphenyl) propyl 1-methyl-2-(3,4-dihydroxyphenyl)ethylamine (Example 2). Only the hydrobromide salts were prepared. Blout et al., U.S. Pat. No. 2,949,359, describe some related compounds including, for example, N-[2-(2,5-dihydroxyphenyl) ethyl-1-methyl-2-(2,5-dihydroxyphenyl)-ethylamine useful in a process for developing photo-sensitive silver halide emulsions. The hydroxyls in the phenyl rings must be ortho or para since oxidation to a quinhydrone or quinone is a requirement for use in such a method. Suh, U.S. Pat. No. 3,932,461 (Suh I) discloses N-[3-(3,4-methylenedioxyphenyl)-1-methylpropyl 2-(3,4-dihydroxyphenyl)ethylamine. Several organic salts are mentioned, including the tartrate. The compounds are said to be depressants or analgesics and to have cardiotonic properties similar to those ascribed to dobutamine (increased contractile force without significant effect on blood pressure or heart rate). No special problem of solubility of the various disclosed salts is mentioned. Another Suh patent, U.S. Pat. No. 3,700,692 (Suh II), discloses similar compounds containing a β-hydroxyethyl-β-(3,4-dihydroxyphenyl)-ethylamine moiety. Biel, U.S. Pat. No. 3,139,441, is another reference disclosing β-hydroxy-ethylamines. Such compounds are derived from norepinephrine rather than dopamine. Finally, Ariens, *Proc. Inter. Pharmacol.* Meeting (Stockholm) 7, 247–64, describes the testing on α and β-receptors of both the norepinephrine-type compounds (Table 1) and the dopamine-type compounds (part of Table III), containing in each instance a 1-methyl-2-(4-hydroxyphenyl)ethyl group attached to an amine group. Salts are not mentioned.

None of the above references relate to the problem of the insolubility of mineral acid salts of dobutamine or of related secondary amines; and none teach the advantageous properties of dobutamine salts formed with certain classes of hydroxyalkanoic acids.

SUMMARY OF THE INVENTION

This invention provides soluble salts of dobutamine formed with hydroxy alkanoic, polyhydroxy alkanoic, hydroxalkandioic and polyhydroxyalkandioic acids having not more than 12 carbon atoms or more than 8 hydroxy groups. Such acids can be represented by the following formula $$(OH)_{1-8}—C_{2-11}\ alkyl—COOH)_{1-2} \qquad I$$

Examples of such acids include lactic acid, gluconic acid, lactobionic acid, glucoheptonic acid, glyceric acid, glycollic acid, tartaric acid, malic acid, mevalonic acid, dihydroxybutyric acid, dihydroxyisobutyric acid, dihydroxyvaleric acid, dihydroxy isovaleric acid, erythronic acid, thereonic acid, bis(hydroxymethyl)malonic acid, 2,3-dihydroxy glutaric acid, dihydroxyadipic acid, bis(hydroxymethyl) acetic acid and the like. Salts of dobutamine formed with optical isomers of the above acids are also included within the scope of this invention.

Dobutamine is a racemate of the following structure:

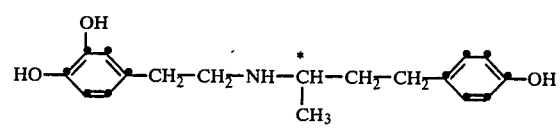

The α-carbon (marked with an asterisk) is asymmetric, yielding two stereoisomers, the (+) and the (−), which, in a 1:1 mixture, form the racemate. This invention includes soluble salts formed with acids of formula I of (+)-N-[3-(4-hydroxyphenyl)-1-methylpropyl]-2-(3,4-dihydroxyphenyl) ethylamine and of the corresponding (−) stereoisomer as well as of the racemate. It will be understood that the term dobutamine as used herein incluudes both the racemate and the disclosed stereoisomers.

The soluble dobutamine salts of this invention can be prepared by direct neutralization of the amine base or by a metathetic reaction involving an acid addition salt of dobutamine. I prefer to use a neutralization procedure.

In the neutralization procedure, dobutamine free base is first prepared by suspending dobutamine hydrochloride in oxygen-free water, adding an antioxidant (peroxide scavenger) followed by the addition of a dilute aqueous solution of a base (an inorganic base such as an alkali metal hydroxide, carbonate, bicarbonate etc. or a water-soluble organic base such as tris (hydroxymethyl)methylamine). Dobutamine base is water-insoluble and separates as a white crystalline mass from the alkaline medium. The crystals are separated, as by filtration, and dried. The dried crystals are then added to oxygen free water containing an anti-oxidant. The desired acid (for salt formation) is added in slight excess as an aqueous solution, and the desired salt is formed. The salt solution can be stored for filling into vials where the solution is lyophilized or the salt solution can first be lyophilized and the lyophilized salt stored.

All the above operations are carried out in an oxygen-free (insofar as practicable) atmosphere.

A typical example of such a reaction sequence follows.

EXAMPLE 1

Preparation of Dobutamine Tartrate

Seventeen grams of dobutamine hydrochloride were suspended in 500 ml of deaerated water [deaerated by alternatively applying a vacuum (10–100 Torr.) followed by a period of sparging with $N_2$]. 150 mg of sodium sulfite were added as a peroxide scavenger. The suspension was stirred under a constant positive $N_2$ pressure. 50 ml of 1N aqueous sodium hydroxide diluted to 120 ml with deaerated water were added in dropwise fashion over a 2.5 hr. period. After the addition was complete, the neutralization mixture was stirred for an additional 2 hours, during which time a white crystalline solid comprising dobutamine free base separated.

The supernate was decanted, and the crystalline residue washed thoroughly with 600 ml of deaerated water. The supernate was again decanted. The solid precipitate was then filtered under $N_2$. The filter cake was washed twice with 100 ml portions of water and was then dried at 45° C. under vacuum for 3 hours. 14.5 g of dobutamine free base were thus obtained.

A repeat preparation was carried out on a 3× scale except that sodium bisulfite (0.5 g) was used in place of sodium sulfite; yield of dried crystalline dobutamine free base=43.0 g (96%).

8.3 Millimoles of dobutamine free base and 8.7 millimoles of one of each of the following acids: glycolic, (+)-tartaric, gluconic, lactobionic and glucoheptonic, were mixed under an $N_2$ atmosphere were an amount of 0.035 g aqueous sodium bisulfite dissolved in water for injection such that the final volume was 25 ml; i.e., 100 mg/ml of dobutamine base. If required, the salt-forming mixture was warmed to expedite solution of dobutamine base. The solid salt can be obtained from the solution, if desired, by evaporation of the solvent.

The solubilities of each of the dobutamine salts thus prepared was in excess of 100 mg/ml. By contrast, a saturated solution of dobutamine hydrochloride provides about 25 mg/ml of dobutamine.

In a repeat with (−) tartaric acid, 58.6 g of dobutamine hydrochloride in deaerated water were neutralized with dilute aqueous sodium hydroxide in the presence of a peroxide scavenger under $N_2$; pH=11.09. The precipitate of dobutamine base was washed with the aerated water and dried. The filter cake was dissolvd in 2 l of deaerated water followed by 26.1 g of (−)-tartaric acid and 0.8 g of sodium bisulfite; pH=3.65. The solution was filtered and then stored at room temperature, always under an $N_2$ atmosphere. Such stored concentrate solutions are stable for 12 months or more at 5° C.

A preferred method of preparing dobutamine free base involves the use of tris(hydroxymethyl)methylamine in place of aqueous sodium hydroxide. A typical preparation using this procedure is carried out as follows: 500 ml of deoxygenated water for injection (WFI) are placed in a 2 l 3-neck round-bottom flask equipped with $N_2$ inlet, dropping funnel, stirring means and a probe leading to a pH meter. A nitrogen sweep is maintained throughout the operation. 50 mg of $NaHSO_3$ are added and the mixture stirred till solution occurs. 80.16 g of dobutamine hydrochloride are added via a y-tube adapter, and any salt remaining in the addition tube is washed in with an additional 500 ml of deoxygenated water (WFI). The resulting slurry is stirred for 15–20 minutes. 250 ml of 1M aqueous tris(hydroxymethyl) methylamine [30.3 g in 250 ml of deoxygenated water (WFI)] are added in dropwise fashion over a 1–2 hr. period at such a rate that the pH of the solution does not rise above pH=8.5. After the addition is completed, the neutralization mixture is chilled to a temperature in the range 0°–10° C. The chilled solution is then vacuum filtered under $N_2$. The filter cake comprising dobutamine free base is washd with 1200 ml of deoxygenated water (WFI) (in three 400 ml portions). Next, a solution is prepared in a 2 l beaker by dissolving 35.56 g of (+)-tartaric acid and 1.3 g of $NaHSO_3$ in 1 l of deoxygenated water (WFI). The filter cake is added with stirring to this solution under $N_2$. After the dobutamine free base has all dissolved, the solution is assayed for dobutamine by UV and the volume of solution now containing the (+)-tartrate salt is adjusted by adding deoxygenated water (WFI) such that the final dobutamine concentration is 50 mg./ml. Five milliliter aliquots are then transferred under $N_2$ to a series of vials. The vials under $N_2$ can be sealed as such or lyophilized and then sealed.

Alternatively, dobutamine free base (the filter cake) can be stored as such and converted to the tartrate salt (or other salt) at a later time in a different area.

In the above preparations, argon can be used in place of nitrogen. In addition, other antioxidants may be used in place of sodium sulfite of sodium bisulfite such as other alkali metal sulfites or bisulfites, thioglycerol, thioerithritol etc.

Although (+)-tartaric and (−) tartaric acids were employed above, (±)-tartaric and mesotartaric acids are also fully operative and form dobutamine salts of high solubility. Furthermore, with any of the acids named, stereoisomers thereof can also be used rather than a racemate. Dobutamine content of all solutions is monitored with UV.

A typical injectable (i.v.) formulation using dobutamine tartrate has the following composition:
250 mg (base equivalent) dobutamine tartrate
4 mg sodium bisulfite
water q.s. to 5 ml.

Such solutions are placed in 5 ml glass ampoules and the ampoule sealed while maintaining an oxygen-free atmosphere. Glass vials with rubber stoppers can be used as well. The ampoules can be opened as needed to provide an i.v. injectable solution for treatment of cardiogenic shock. Alternatively, the solutions can be lyophilized and reconstituted with WFI prior to use.

I claim:

1. A salt of (±)-N-[3-hydroxyphenyl)-1-methylpropyl]-2-(3,4-dihydroxyphenyl) ethylamine formed with an acid selected from the group consisting of glycolic acid, lactobionic acid, tartaric acid, lactic acid, gluconic acid, and glucoheptahoic acid.

2. A salt according to claim 1, said salt being a racemic dobutamine tartrate.

3. A salt according to claim 1, said salt being racemic dobutamine (+)-tartrate.

4. A salt according to claim 1, said salt being racemic dobutamine (−)-tartrate.

5. A salt according to claim 1, said salt being racemic dobutamine glucoheptonate.

6. A salt according to claim 1, said salt being racemic dobutamine lactate.

7. A salt according to claim 1, said salt being racemic dobutamine lactobionate.

8. A salt according to claim 1, said salt being racemic dobutamine gluconate.

9. A salt according to claim 1, said salt being racemic dobutamine glycolate.

10. A pharmaceutical formulation for the treatment of cardiogenic shock comprising a dobutamine salt according to claim 1 with a water carrier.

11. A formulation according to claim 10 in which the salt is racemic dobutamine tartrate.

12. A formulation according to claim 10 in which the salt is racemic dobutamine lactobionate.

13. A salt of (−) N-[3-(4-hydroxyphenyl)-1-methylpropyl]-2-(3,4-dihydroxyphenyl) ethylamine formed with an acid selected from the group consisting of glycolic acid, tartaric acid, (+)-lactic acid, gluconic acid, and lactobionic acid.

14. A salt according to claim 13, said salt being (−) dobutamine glycolate.

15. A salt according to claim 13, said salt being (−)-dobutamine tartrate.

16. A salt according to claim 13, said salt being (−)-dobutamine-(+)-lactate.

17. A salt according to claim 13, said salt being (−)-dobutamine gluconate.

18. A salt according to claim 13, said salt being (−)-dobutamine lactobionate.

19. A pharmaceutical formulation for the treatment of cardiogenic shock comprising a dobutamine salt according to claim 13 with a water carrier.

20. A formulation according to claim 19 in which the salt is (−)-dobutamine lactobionate.

21. A salt of (+) N-[3-(4-hydroxyphenyl)-1-methylpropyl]-2-(3,4-dihydroxyphenyl) ethylamine formed with an acid selected from the group consisting of glycolic acid, (+)- lactic acid, gluconic acid, and lactobionic acid.

22. A salt according to claim 21, said salt being (+)-dobutamine glycolate.

23. A salt according to claim 21, said salt being (+)-dobutamine lactobionate.

24. A salt according to claim 21, said salt being (+)-dobutamine-(+)-lactate.

25. A salt according to claim 21, said salt being (+)-dobutamine gluconate.

26. A pharmaceutical formulation for the treatment of cardiogenic shock comprising a dobutamine salt according to claim 21 with a water carrier.

27. A formulation according to claim 26 in which the salt is (+)-dobutamine lactobionate.

* * * * *

UNITED STATES PATENT AND TRADEMARK OFFICE
CERTIFICATE OF CORRECTION

PATENT NO. : 4,704,407
DATED : November 3, 1987
INVENTOR(S) : Eddie H. Massey

It is certified that error appears in the above—identified patent and that said Letters Patent is hereby corrected as shown below:

Column 1, line 63, the formula which reads "$(OH)_{1-8}-C_{2-11} alkyl-COOH)_{1-2}$" should read --$(OH)_{1-8}-(C_{2-11} alkyl)-(COOH)_{1-2}$--.

Column 2, line 2, "thereonic acid" should read --threonic acid--.

Column 4, line 33, in Claim 1, "($\pm$)-N-[3-hydroxyphenyl)-1-methyl" should read --($\pm$)-N-[3-(4-hydroxyphenyl-1-methyl- --.

Column 4, line 37, in Claim 1, "glucoheptahoic acid" should read --glucoheptonic acid--.

Column 4, lines 67 and 68, in Claim 14, "(-)dobutamine glycolate" should read -- (-)-dobutamine glycolate--.

Signed and Sealed this

Eleventh Day of October, 1988

Attest:

DONALD J. QUIGG

Attesting Officer

Commissioner of Patents and Trademarks